US007689271B1

(12) United States Patent  (10) Patent No.: US 7,689,271 B1
Sullivan  (45) Date of Patent: Mar. 30, 2010

(54) NON-INVASIVE HEART RATE AND RESPIRATION MEASUREMENTS FROM EXTREMITIES

(75) Inventor: Patrick K. Sullivan, Honolulu, HI (US)

(73) Assignee: Hoana Medical, Inc., Honolulu, HI (US)

( * ) Notice: Subject to any disclaimer, the term of this patent is extended or adjusted under 35 U.S.C. 154(b) by 1530 days.

(21) Appl. No.: 10/876,547

(22) Filed: Jun. 28, 2004

Related U.S. Application Data

(60) Provisional application No. 60/482,436, filed on Jun. 26, 2003.

(51) Int. Cl.
*A61B 5/04* (2006.01)
(52) U.S. Cl. .................................................. 600/512
(58) Field of Classification Search ................ 600/484, 600/529, 535
See application file for complete search history.

(56) References Cited

U.S. PATENT DOCUMENTS

| | | | |
|---|---|---|---|
| 3,926,177 A | 12/1975 | Hardway, Jr. et al. | |
| 3,996,922 A | 12/1976 | Basham | |
| 4,033,332 A | 7/1977 | Hardway, Jr. et al. | |
| 4,320,766 A | 3/1982 | Alihanka et al. | |
| 4,438,771 A * | 3/1984 | Friesen et al. | 600/484 |
| 4,513,748 A | 4/1985 | Nowogrodzki et al. | |
| RE32,180 E | 6/1986 | Lewiner et al. | |
| 4,657,026 A | 4/1987 | Tagg | |
| 4,686,999 A | 8/1987 | Snyder et al. | |
| 4,889,131 A | 12/1989 | Salem et al. | |
| 5,002,060 A | 3/1991 | Nedivi | |
| 5,448,996 A * | 9/1995 | Bellin et al. | 600/574 |
| 5,479,932 A | 1/1996 | Higgins et al. | |
| 5,590,650 A * | 1/1997 | Genova | 600/301 |
| 5,620,003 A * | 4/1997 | Sepponen | 600/527 |
| 5,684,460 A | 11/1997 | Scanlon | |
| 5,807,267 A | 9/1998 | Bryars et al. | |
| 5,911,158 A * | 6/1999 | Henderson et al. | 73/583 |
| 5,964,720 A * | 10/1999 | Pelz | 600/595 |
| 6,047,203 A | 4/2000 | Sackner et al. | |
| 6,375,621 B1 * | 4/2002 | Sullivan | 600/484 |
| 6,547,743 B2 | 4/2003 | Brydon | |
| 6,702,752 B2 | 3/2004 | Dekker | |
| 2004/0111045 A1 | 6/2004 | Sullivan et al. | |

FOREIGN PATENT DOCUMENTS

| | | | |
|---|---|---|---|
| GB | 2252827 | | 8/1982 |
| GB | 2138144 | | 10/1984 |
| GB | 2166871 | | 5/1986 |
| WO | WO 03/087737 | * | 9/2003 |

* cited by examiner

*Primary Examiner*—Mark W Bockelman
*Assistant Examiner*—Roland Dinga
(74) *Attorney, Agent, or Firm*—James Creighton Wray; Meera P. Narasimhan

(57) ABSTRACT

The invention determines the heart rate and respiration rate of a patient through the patient's extremities. Heart rate and respiration rate are determined via an energy spectrum, periodogram or histogram using a time series analysis. A patient can stand near the device and lean on it, or stand on a piezoelectric pad. A microcomputer provides calculations to determine heart and respiratory rates using signal processing and time series analysis of data.

23 Claims, 2 Drawing Sheets

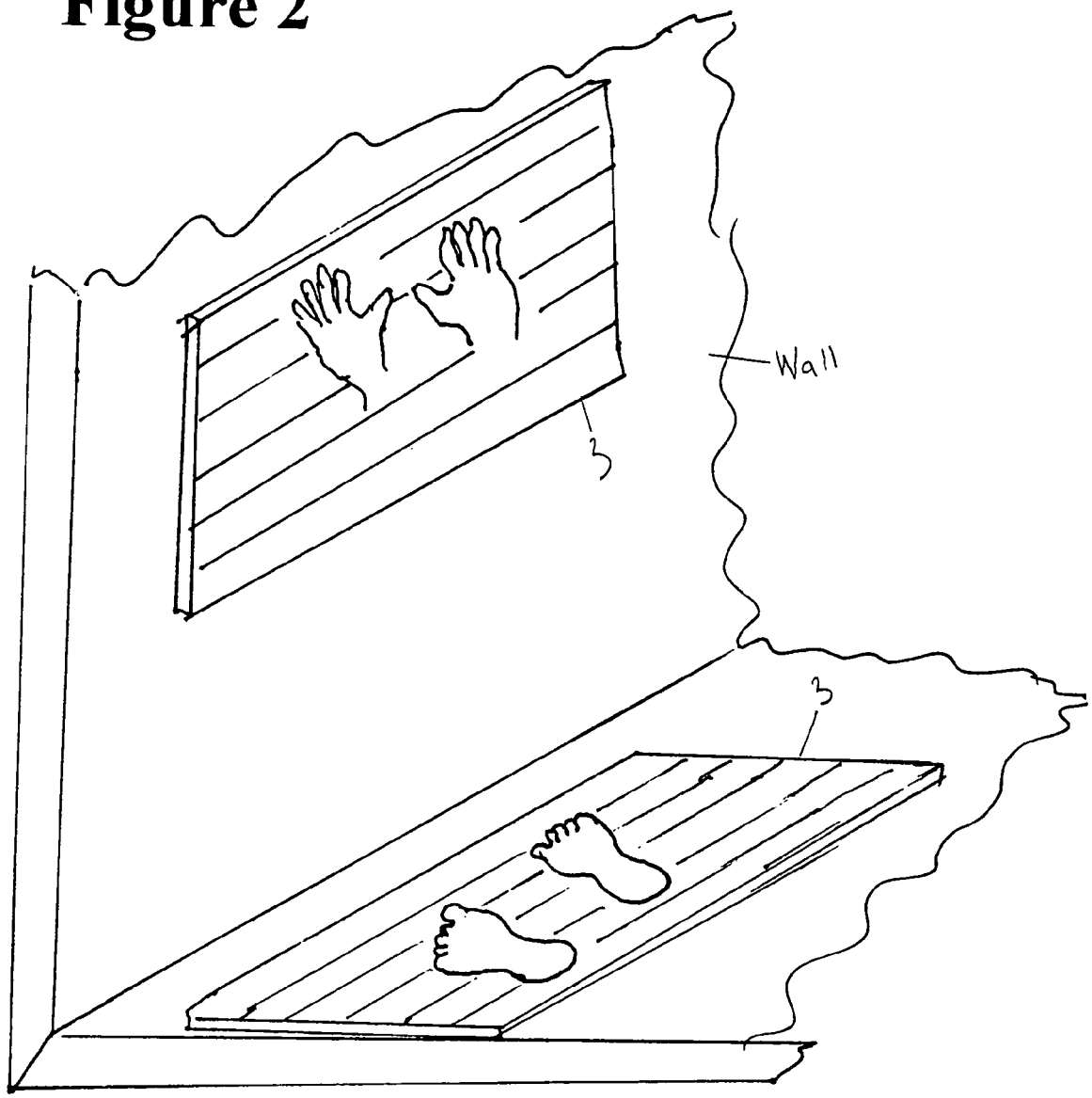

NON-INVASIVE HEART RATE AND RESPIRATION MEASUREMENTS FROM EXTREMITIES

BACKGROUND OF THE INVENTION

This application claims the benefit of U.S. Provisional Application No. 60/482,436 filed Jun. 26, 2003.

Current methods for measurement of blood pressure and other vital signs are inefficient. Many measurements of patient vital signs are invasive procedures that are uncomfortable for the patient. Additionally, current methods do not provide for adequate continuous, real-time monitoring of a patient's condition.

Needs exist for improved methods of non-invasive blood pressure measurements.

SUMMARY OF THE INVENTION

The present invention determines heart rate and respiration rate through a patient's extremities. Heart rate and respiration rate are determined via an energy spectrum, periodogram or histogram using a time series analysis. The present invention can also measure and monitor other vital signs of a patient. A patient can stand near the device and lean on it, or stand on a piezoelectric pad. A microcomputer provides calculations to determine heart and respiratory rates using signal processing and time series analysis of data.

The heart rate and respiration rate monitoring device of the present invention includes at least one piezoelectric pad or body that contacts a patient's body. The patient can stand near the device and lean on it or stand on the device if it is on the floor. The monitoring device can contact the patient's feet or hands or any other appropriate extremities.

A discretized sensing array is located on a surface of the piezoelectric pad or body. The discretized sensing array collects acoustic, electromechanical or other physiological signals emanating from the patient's body. The discretized sensing array picks up these signals and transmits them as voltage signals from the discretized sensing array to a receiving and computing device. The transmission system can be wire, fiber optic or wireless. The signal can be digitized with an analog-to-digital converter resulting in a digitized voltage versus digitized time signal. The digitized signal can be used to calculate heart rate and respiration rate by means of time frequency analysis or other similar methods, such as autocovariance, fast Fourier transform and other methods.

Once at the computing device, a value for the heart rate and respiration rate of a patient are determined using time frequency analysis or other similar analysis methods.

Additionally, the present invention can incorporate a scale or weighing machine. The patient stands on the piezoelectric pad or body and the patient's weight, heart rate and respiration rate, or any combination thereof, are measured.

These and further and other objects and features of the invention are apparent in the disclosure, which includes the above and ongoing written specification, with the claims and the drawings.

BRIEF DESCRIPTION OF THE DRAWINGS

FIG. 2 is a diagram of alternative configurations for the monitoring system.

DETAILED DESCRIPTION OF THE PREFERRED EMBODIMENTS

Figure 1:
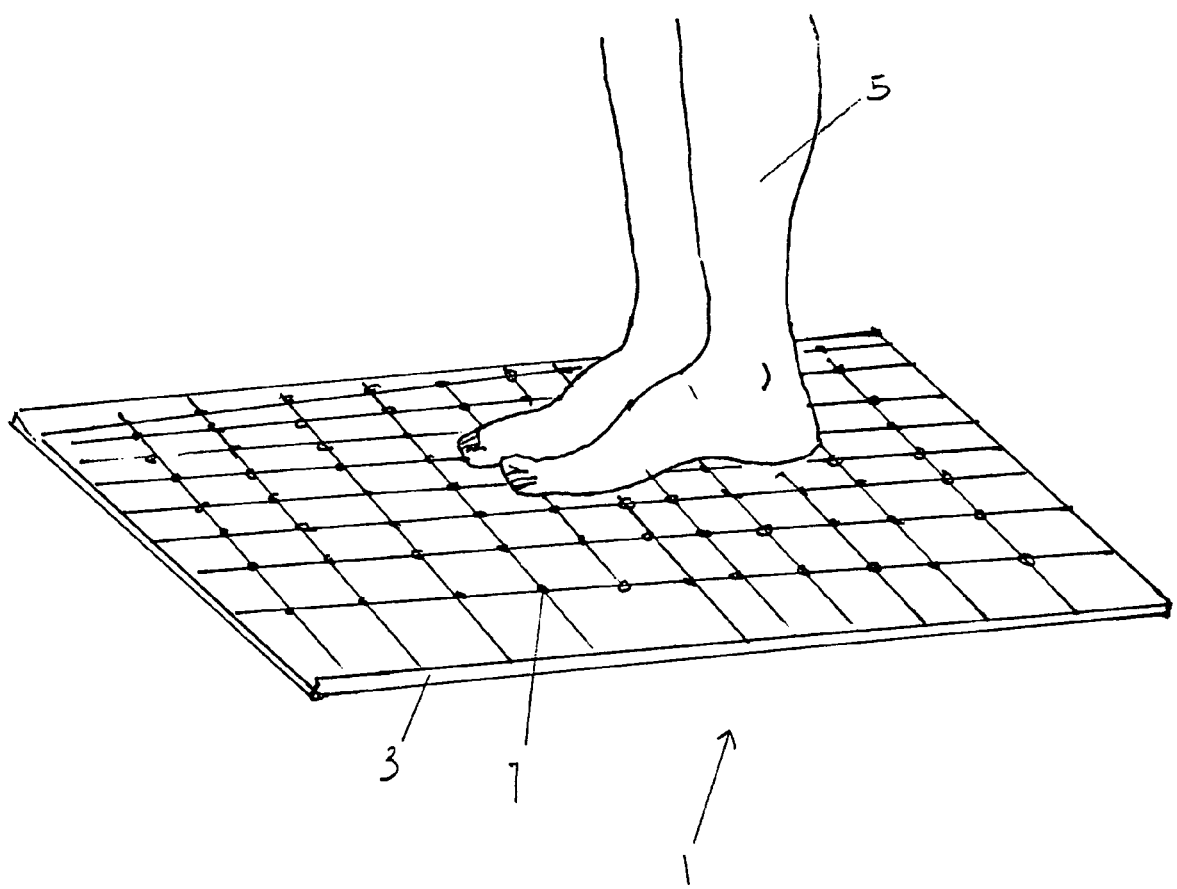
FIG. 1 is a diagram of the monitoring system with a discretized array.

The present invention determines heart rate and respiration rate through a patient's extremities. Heart rate and respiration rate are determined via an energy spectrum, periodogram or histogram using a time series analysis. The present invention can also measure and monitor other vital signs of a patient. A patient can stand near the device and lean on it, or stand on a piezoelectric pad. A microcomputer provides calculations to determine heart and respiratory rates using signal processing and time series analysis of data.

The heart rate and respiration rate monitoring device 1 of the present invention can be seen in FIG. 1, and includes at least one piezoelectric pad or body 3 that contacts a patient's body 5. The piezoelectric pad or body 3 can vary in size and thickness depending on the needs of the user. Preferably, the piezoelectric pad or body 3 is a thin pad that is flexible and mobile. The patient 5 can stand near the device 1 and lean on it or stand on the device if it is on the floor, as shown in FIG. 2. The monitoring device 1 can contact the patient's feet or hands or any other appropriate extremities or be in close contact to the patient's body. The positions shown in FIG. 2 are alternative configurations; the patient can either stand on a pad or lean on a pad mounted on a wall.

A discretized sensing array 7 is located on a surface of the piezoelectric pad or body 3. The discretized sensing array 7 collects acoustic, electromechanical or other physiological signals emanating from the patient's body 5. The discretized sensing array 7 picks up these signals and transmits them as voltage signals from the discretized sensing array to a receiving and computing device. The transmission system can be wire, fiber optic or wireless. The monitoring system of the present invention provides continuous, real-time measurement and analysis of a patient's heart rate and respiration rate while the patient is in proximity to the sensing device.

Further, the signal can be digitized with an analog-to-digital converter resulting in a digitized voltage versus digitized time signal. The digitized signal can be used to calculate heart rate and respiration rate by means of time frequency analysis or other similar methods, such as autocovariance, fast Fourier transform or other methods.

Once at the computing device, a value for the heart rate and respiration rate of a patient are determined using time frequency analysis methods. Time series data is analyzed to produce energy spectra for each location that the patient's body contacts the discretized sensing array 7. This data is then used to determine heart rate, respiration rate or other vital signs.

Additionally, the present invention can incorporate a scale or weighing machine. The patient 5 stands on the piezoelectric pad or body 3, and the patient's weight, heart rate and respiration rate, or any combination thereof, are measured.

While the invention has been described with reference to specific embodiments, modifications and variations of the invention may be constructed without departing from the scope of the invention, which is defined in the following claims.

The invention claimed is:

1. A heart rate and respiration rate monitoring method comprising:
   providing at least one piezoelectric pad,
   providing one or more surfaces on the at least one piezoelectric pad for contacting a patient's feet or hand extremities with the piezoelectric pad,
   providing one or more discretized sensor arrays on the one or more surfaces of the piezoelectric pad, contacting the patient's feet or hand extremities to the one or more discretized sensor arrays by leaning on or standing on and thereby contacting the one or more discretized sensor arrays, collecting discretized acoustic, electromechanical or other physiological signals with the discretized sensing array, converting the discretized acoustic, electromechanical or other physiological signals into discretized voltage signals, transmitting the discretized voltage signals from the discretized sensing array to a receiving and computing device, calculating a value for the heart rate and respiration rate of a patient via analyzing time series data and producing energy spectra for each location that the patient's feet or hand extremities contact the discretized sensor array.

2. The method of claim 1, further comprising measuring and monitoring other vital signs of a patient.

3. The method of claim 1, wherein the at least one piezoelectric pad is sized in proportion to the extremity being contacted.

4. The method of claim 1, wherein the at least one piezoelectric pad is in direct contact with the patient's extremities.

5. The method of claim 1, wherein the discretized sensing array is regular.

6. The method of claim 1, wherein the discretized sensing array is irregular.

7. The method of claim 1, further comprising digitizing the voltage signal with an analog-to-digital converter and employing a digitized voltage versus digitized time signal.

8. The method of claim 7, wherein the digitizing further comprises providing a time series.

9. The method of claim 1, wherein the time series analysis methods are autocovariance, fast Fourier transform or another method.

10. The method of claim 1, wherein the transmitting of signals comprises transmitting voltage signals via wire, fiber optics or wirelessly.

11. The method of claim 1, further comprising integrating a scale or weighing machine for measuring weight, heart rate and respiration rate of a patient or any combination thereof.

12. A heart rate and respiration rate monitoring device comprising:
   one piezoelectric pad having a size to receive feet or hands of a patient,
   a surface of the one piezoelectric pad for contacting the patient's extremities,
   a discretized sensing array grid on a surface of the piezoelectric pad for collecting discretized acoustic, electromechanical or other physiological signals and converting the discretized acoustic, electromechanical or other physiological signals into discretized voltage signals,
   a transmission system for transmitting the discretized voltage signals from the discretized sensing array grid to a receiving and computing device,
   a computing device for receiving the discretized voltage signals and determining a value for the heart rate and respiration rate of a patient by analyzing time series data and producing energy spectra for each location that the patient's body contacts the discretized sensor array.

13. The device of claim 12, wherein other vital signs of a patient are measured and monitored.

14. The device of claim 12, wherein the at least one piezoelectric pad is sized in proportion to the extremity being contacted.

15. The device of claim 12, wherein the at least one piezoelectric pad is in direct contact with the patient's extremities.

16. The device of claim 12, wherein the discretized sensing array is regular.

17. The device of claim 12, wherein the discretized sensing array is irregular.

18. The device of claim 12, further comprising an analog-to-digital converter for digitizing the voltage signal and for employing a digitized voltage versus digitized time signal.

19. The device of claim 18, wherein the digitizing further comprises providing a time series.

20. The device of claim 12, wherein the time series analysis methods are autocovariance, fast Fourier transform or another method.

21. The device of claim 12, wherein the transmission system transmits voltage signals via wire, fiber optics or wirelessly.

22. The device of claim 12, further comprising a scale or weighing machine for measuring weight, heart rate and respiration rate of a patient or any combination thereof.

23. A heart rate and respiration rate monitoring method comprising:
   providing at least one piezoelectric pad,
   providing one or more surfaces on the at least one piezoelectric pad for contacting a patient's feet or hand extremities with the piezoelectric pad,
   providing one or more discretized sensor arrays on the one or more surfaces of the piezoelectric pad,
   contacting the patient's feet or hand extremities to the one or more discretized sensor arrays by leaning on or standing on and thereby contacting the one or more discretized sensor arrays,
   collecting discretized acoustic, electromechanical or other physiological signals with the discretized sensing array,
   converting the discretized acoustic, electromechanical or other physiological signals into discretized voltage signals,
   transmitting the discretized voltage signals from the discretized sensing array to a receiving and computing device,
   calculating a value for the heart rate and respiration rate of a patient via analyzing time series data where the patient's feet or hand extremities contact the discretized sensor array.

* * * * *